(12) United States Patent
Burdeniuc et al.

(10) Patent No.: US 7,495,131 B2
(45) Date of Patent: Feb. 24, 2009

(54) BLOWING CATALYST COMPOSITIONS CONTAINING HYDROXYL AND SURFACE ACTIVE GROUPS FOR THE PRODUCTION OF POLYURETHANE FOAMS

(75) Inventors: Juan Jesus Burdeniuc, Macungie, PA (US); Ann Zdancewic Kamzelski, Schwenksville, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 468 days.

(21) Appl. No.: 11/083,452

(22) Filed: Mar. 18, 2005

(65) Prior Publication Data

US 2006/0211783 A1 Sep. 21, 2006

(51) Int. Cl.
*C07C 215/06* (2006.01)
(52) U.S. Cl. ........................ 564/503; 502/167; 564/463; 564/508; 564/511; 564/512
(58) Field of Classification Search ................ 564/463, 564/503, 508, 511, 512; 502/167
See application file for complete search history.

(56) References Cited

U.S. PATENT DOCUMENTS

| 3,836,488 | A |  | 9/1974 | Pruitt et al. |  |
|---|---|---|---|---|---|
| 4,026,840 | A |  | 5/1977 | Bechara et al. |  |
| 4,143,003 | A |  | 3/1979 | Haas et al. |  |
| 4,148,762 | A |  | 4/1979 | Koch et al. |  |
| 5,039,713 | A |  | 8/1991 | Petrella |  |
| 5,229,430 | A |  | 7/1993 | Tamano et al. |  |
| 5,508,314 | A | * | 4/1996 | Listemann et al. | ........... 521/115 |
| 5,633,293 | A | * | 5/1997 | Van Court Carr et al. | ... 521/118 |
| 5,681,867 | A |  | 10/1997 | Brown |  |
| 6,187,957 | B1 | * | 2/2001 | Meyer et al. | ................. 564/473 |
| 6,777,456 | B2 | * | 8/2004 | Kiso et al. | ................... 521/129 |
| 7,064,172 | B2 | * | 6/2006 | Masuda et al. | ................. 528/53 |

FOREIGN PATENT DOCUMENTS

| JP | 2000-297132 | * | 10/2000 |
| WO | 01/58976 |  | 8/2001 |
| WO | 2004/113410 |  | 12/2004 |

* cited by examiner

*Primary Examiner*—John Cooney
(74) *Attorney, Agent, or Firm*—Michael Leach

(57) ABSTRACT

Tertiary amines useful as catalysts for preparing polyurethane foams are provided. Tertiary amines are employed to catalyze the trimerization reaction of isocyanates and the reaction between isocyanates and active hydrogen-containing compounds, such as a polyol and/or a blowing agent. Such tertiary amine has the general formula

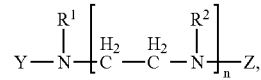

wherein $R^1$, $R^2$, Y, Z, and n are defined herein.

12 Claims, No Drawings

BLOWING CATALYST COMPOSITIONS CONTAINING HYDROXYL AND SURFACE ACTIVE GROUPS FOR THE PRODUCTION OF POLYURETHANE FOAMS

BACKGROUND OF THE INVENTION

The present invention relates to tertiary amines containing hydroxyl and surface active groups and the use thereof as catalysts for preparing polyurethane foams.

Polyurethane foams are widely known and used in the automotive, housing, and other industries. Such foams are produced by the reaction of a polyisocyanate with a polyol in the presence of various additives. One such additive is a chlorofluorocarbon (CFC) blowing agent which vaporizes as a result of the reaction exotherm causing the polymerizing mass to form a foam. The discovery that CFCs deplete ozone in the stratosphere has resulted in mandates diminishing CFC use. Production of water blown foams, in which blowing is performed with $CO_2$ generated by the reaction of water with the polyisocyanate, has therefore become increasingly important. Tertiary amine catalysts are typically used to accelerate blowing, for example, the reaction of water with polyisocyanate to generate $CO_2$, and gelling, for example, the reaction of a polyol with isocyanate.

The ability of the tertiary amine catalyst to selectively promote either blowing or gelling is an important consideration in selecting a catalyst for the production of a particular polyurethane foam. If a catalyst promotes the blowing reaction to a too high degree, much of the $CO_2$ will be evolved before sufficient reaction of isocyanate with polyol has occurred, and the $CO_2$ will bubble out of the formulation, resulting in a collapse of the polymerization mass and yielding a foam of poor quality. In contrast, if a catalyst too strongly promotes the gelling reaction, a substantial portion of the $CO_2$ will be evolved after a significant degree of polymerization has occurred. Again, poor quality foams which are characterized by high density, broken or poorly defined cells, or other undesirable features, will be produced.

Tertiary amine catalysts generally are malodorous and offensive and many have high volatility due to their low molecular weight. Release of tertiary amine during foam processing may present significant safety and toxicity problems, and release of residual amine from customer products is generally undesirable. On the other hand, low vapor pressure-high molecular weight amine catalysts are expected to require very high catalyst usage due to their low nitrogen/carbon ratio, making the manufacturing cost too high.

Amine catalysts which contain hydroxyl groups, as well as $C_6$ or higher alkyl or fatty acid groups have shown good activity, making their usage level relatively modest despite their high molecular weight. Further, their high molecular weight, reduced volatility, and reduced odor can limit the exposure of operators and end users to offensive amine vapors. In addition, amine catalysts containing hydroxyl functionality can chemically bind into the urethane during the reaction, thus limiting their release from the finish product. Amine catalysts containing secondary hydroxyl functionality are generally preferred because they exhibit a desirable balance between their promotion of the active hydrogen-isocyanate reaction (gelling and blowing) and their own reactivity with isocyanates. It is therefore desirable to produce new tertiary amines and catalyst systems employing such tertiary amines that have increased catalytic activity, decreased usage levels, and increased ability to bind to the urethane matrix. It is also desirable to provide a method for producing polyurethane foams which employs such tertiary amine catalyst systems. It is to these ends that the present invention is directed.

BRIEF SUMMARY OF THE INVENTION

The present invention relates to novel tertiary amines useful as catalysts for preparing polyurethane foams. These tertiary amines can catalyze the trimerization reaction of isocyanates and, as well, the reaction between isocyanates and active hydrogen-containing compounds, such as a polyol and/or water. The tertiary amine has the general formula

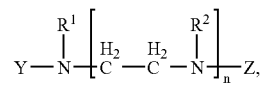

wherein
$R^1$ and $R^2$ are, independently, an alkyl group having from 1 to 3 carbon atoms;
Y is

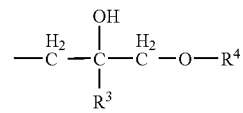

or an alkyl group having from 1 to 3 carbon atoms;
Z is

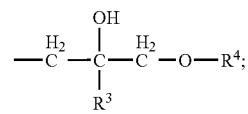

$R^3$ is hydrogen, an alkyl group having from 1 to about 10 carbon atoms, or an alkenyl group having from one to about ten carbon atoms;
$R^4$ is a substituted or unsubstituted alkyl group having from 1 to about 36 carbon atoms, a substituted or unsubstituted alkenyl group having from 1 to about 36 carbon atoms, or an acyl group having the general formula —CO—$R^5$;
$R^5$ is hydrogen, a substituted or unsubstituted alkyl group having from 1 to about 35 carbon atoms, or an alkenyl group having from 1 to about 35 carbon atoms; and
n is an integer from 1 to 7, inclusive.

The present invention also relates to a method for preparing polyurethane foams, which comprises contacting at least one organic isocyanate compound, at least one polyol, at least one blowing agent, and a tertiary amine catalyst composition. The present invention further provides a method for catalyzing the reaction between at least one isocyanate compound and at least one active hydrogen-containing compound, such as a polyol and/or water. The present invention also encompasses a method for catalyzing the trimerization reaction of isocyanate compounds.

DETAILED DESCRIPTION OF THE INVENTION

The present invention provides a novel tertiary amine catalyst useful for making polyurethane foams. One aspect of the present invention comprises a tertiary amine compound which catalyzes the reaction between at least one isocyanate compound and at least one active hydrogen-containing compound, such as a polyol and/or water. Another aspect of the present invention is directed to a tertiary amine compound which catalyzes the trimerization of isocyanate compounds. The present invention also provides a method for making polyurethane foams using tertiary amine catalyst compositions containing hydroxyl and surface active groups. Yet another aspect of the present invention encompasses producing polyurethane foams by contacting at least one isocyanate compound, at least one polyol compound, at least one blowing agent, and at least one tertiary amine catalyst composition. A further aspect of this invention is directed to a method for catalyzing the reaction between at least one isocyanate compound and at least one active hydrogen-containing compound, such as a polyol and/or a blowing agent. Another aspect of the present invention encompasses a method for catalyzing the trimerization reaction of isocyanate compounds.

The Tertiary Amine Catalyst Composition

Catalyst compositions in accordance with the present invention catalyze the trimerization reaction of isocyanates and the reaction between isocyanates and active hydrogen-containing compounds. The active hydrogen-containing compound can be, for example, an alcohol, a polyol, an amine, or water. Accordingly, the catalyst composition can promote, among other reactions, the gelling reaction of polyols with isocyanate to produce polyurethane, the blowing reaction of water with isocyanate to release carbon dioxide, the trimerization of isocyanate compounds, or all three reactions.

In one aspect of the present invention, the tertiary amine catalyst composition has the general formula $$Y-N\begin{matrix}R^1\\|\end{matrix}\left[\begin{matrix}H_2&H_2&R^2\\C-C-N\\\end{matrix}\right]_n Z,$$

wherein $R^1$ and $R^2$ are, independently, an alkyl group having from 1 to 3 carbon atoms;

Y is

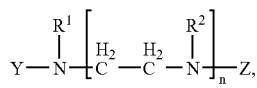

or an alkyl group having from 1 to 3 carbon atoms;

Z is

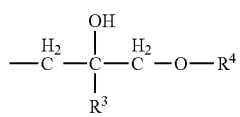

$R^3$ is hydrogen, an alkyl group having from 1 to about 10 carbon atoms, or an alkenyl group having from one to about ten carbon atoms;

$R^4$ is a substituted or unsubstituted alkyl group having from 1 to about 36 carbon atoms, a substituted or unsubstituted alkenyl group having from 1 to about 36 carbon atoms, or an acyl group having the general formula —CO—$R^5$;

$R^5$ is hydrogen, a substituted or unsubstituted alkyl group having from 1 to about 35 carbon atoms, or an alkenyl group having from 1 to about 35 carbon atoms; and n is an integer from 1 to 7, inclusive.

In another aspect of the present invention, $R^1$ and $R^2$ are methyl groups;

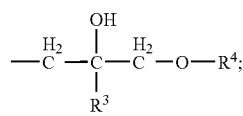

Y is a methyl group or $R^3$ is hydrogen;

$R^4$ is a substituted or unsubstituted alkyl group having from 1 to about 18 carbon atoms, a substituted or unsubstituted alkenyl group having from 1 to about 18 carbon atoms, or an acyl group having the general formula —CO—$R^5$;

$R^5$ is hydrogen or a substituted or unsubstituted alkyl group having from 1 to about 17 carbon atoms, or an alkenyl group having from 1 to about 17 carbon atoms; and n is an integer from 2 to 7, inclusive, or an integer from 1 to 3, inclusive.

Catalyst compositions in accordance with the present invention can be prepared by reacting an alkyl glycidyl ether with an ethyleneamine. Examples of suitable ethyleneamines include, but are not limited to, diethylenetriamine (DETA), triethylenetetramine (TETA), tetraethylenepentamine (TEPA), and pentaethylenehexamine (PEHA). Examples of suitable alkyl glycidyl ethers include, but are not limited to, alkly glycidyl ethers wherein the alkyl group has from 1 to about 35 carbon atoms. The alkyl group can be, for example, octadecyl, heptadecyl, hexadecyl, pentadecyl, tetradecyl, tridecyl, dodecyl, undecyl, decyl, nonyl, octyl, heptyl, hexyl, pentyl, butyl, ethyl, or methyl. The unreacted amine may be removed by distillation and the product reacted with formaldehyde and pressurized hydrogen at a temperature of about 60 to about 120° C. in the presence of a metal catalyst, such as 5% palladium on carbon.

Various alkyl glycidyl ethers are available commercially from the Air Products and Chemicals, Inc. Epodil® product line, for example, Epodile® 746 and Epodil® 748. Epodil® products are particularly advantageous in the present invention because they contain from about 0.1 to about 2 wt % hydrolysable chloride ions. Similarly, other alkyl glycidyl ethers containing hydrolysable chloride ions may be used in the present invention. As discussed in PCT/2004/113410 to Dow Global Technologies, Inc., incorporated herein by reference in its entirety, the presence of a small amount of hydrolysable chloride ions during the polymerization reaction may serve to improve the humid aging properties of the final polyurethane foam product.

In one aspect of the present invention, tertiary amine catalyst compositions of this invention include, but are not limited to N-(2-hydroxypropyl-octadecyl ether)-N,N',N'',N''',N'''' pentamethyltriethylenetetramine;

N-(2-hydroxypropyl-heptadecyl ether)-N,N',N'',N''',N'''' pentamethyltriethylenetetramine;

N-(2-hydroxypropyl-hexadecyl ether)-N,N',N'',N''',N'''' pentamethyltriethylenetetramine;

N-(2-hydroxypropyl-pentadecyl ether)-N,N',N'',N''',N'''' pentamethyltriethylenetetramine;
N-(2-hydroxypropyl-tetradecyl ether)-N,N',N'',N''',N'''' pentamethyltriethylenetetramine;
N-(2-hydroxypropyl-tridecyl ether)-N,N',N'',N''',N'''' pentamethyltriethylenetetramine;
N-(2-hydroxypropyl-dodecyl ether)-N,N',N'',N''',N'''' pentamethyltriethylenetetramine;
N-(2-hydroxypropyl-undecyl ether)-N,N',N'',N''',N'''' pentamethyltriethylenetetramine;
N-(2-hydroxypropyl-decyl ether)-N,N',N'',N''',N'''' pentamethyltriethylenetetramine;
N-(2-hydroxypropyl-nonyl ether)-N,N',N'',N''',N'''' pentamethyltriethylenetetramine;
N-(2-hydroxypropyl-octyl ether)-N,N',N'',N''',N'''' pentamethyltriethylenetetramine;
N-(2-hydroxypropyl-heptyl ether)-N,N',N'',N''',N'''' pentamethyltriethylenetetramine;
N-(2-hydroxypropyl-hexyl ether)-N,N',N'',N''',N'''' pentamethyltriethylenetetramine;
N-(2-hydroxypropyl-pentyl ether)-N,N',N'',N''',N'''' pentamethyltriethylenetetramine;
N-(2-hydroxypropyl-butyl ether)-N,N',N'',N''',N'''' pentamethyltriethylenetetramine;
N-(2-hydroxypropyl-ethyl ether)-N,N',N'',N''',N'''' pentamethyltriethylenetetramine;
N-(2-hydroxypropyl-methyl ether)-N,N',N'',N''',N'''' pentamethyltriethylenetetramine;
N-(2-hydroxypropyl-octadecyl ether)-N,N',N'',N''' tetramethyldiethylenetriamine;
N-(2-hydroxypropyl-heptadecyl ether)-N,N',N'',N''' tetramethyldiethylenetriamine;
N-(2-hydroxypropyl-hexadecyl ether)-N,N',N'',N''' tetramethyldiethylenetriamine;
N-(2-hydroxypropyl-pentadecyl ether)-N,N',N'',N''' tetramethyldiethylenetriamine;
N-(2-hydroxypropyl-tetradecyl ether)-N,N',N'',N''' tetramethyldiethylenetriamine;
N-(2-hydroxypropyl-tridecyl ether)-N,N',N'',N''' tetramethyldiethylenetriamine;
N-(2-hydroxypropyl-dodecyl ether)-N,N',N'',N''' tetramethyldiethylenetriamine;
N-(2-hydroxypropyl-undecyl ether)-N,N',N'',N''' tetramethyldiethylenetriamine;
N-(2-hydroxypropyl-decyl ether)-N,N',N'',N''' tetramethyldiethylenetriamine;
N-(2-hydroxypropyl-nonyl ether)-N,N',N'',N''' tetramethyldiethylenetriamine;
N-(2-hydroxypropyl-octyl ether)-N,N',N'',N''' tetramethyldiethylenetriamine;
N-(2-hydroxypropyl-heptyl ether)-N,N',N'',N''' tetramethyldiethylenetriamine;
N-(2-hydroxypropyl-hexyl ether)-N,N',N'',N''' tetramethyldiethylenetriamine;
N-(2-hydroxypropyl-pentyl ether)-N,N',N'',N''' tetramethyldiethylenetriamine;
N-(2-hydroxypropyl-butyl ether)-N,N',N'',N''' tetramethyldiethylenetriamine;
N-(2-hydroxypropyl-ethyl ether)-N,N',N'',N''' tetramethyldiethylenetriamine;
N-(2-hydroxypropyl-methyl ether)-N,N',N'',N''' tetramethyldiethylenetriamine; or any combination thereof.

In another aspect of the present invention, tertiary amine catalyst compositions of this invention include, but are not limited to
N-(2-hydroxypropyl-octadecyl ether)-N,N',N'',N''',N'''' pentamethyltriethylenetetramine;
N-(2-hydroxypropyl-hexadecyl ether)-N,N',N'',N''',N'''' pentamethyltriethylenetetramine;
N-(2-hydroxypropyl-tetradecyl ether)-N,N',N'',N''',N'''' pentamethyltriethylenetetramine;
N-(2-hydroxypropyl-dodecyl ether)-N,N',N'',N''',N'''' pentamethyltriethylenetetramine;
N-(2-hydroxypropyl-decyl ether)-N,N',N'',N''',N'''' pentamethyltriethylenetetramine;
N-(2-hydroxypropyl-octyl ether)-N,N',N'',N''',N'''' pentamethyltriethylenetetramine;
N-(2-hydroxypropyl-hexyl ether)-N,N',N'',N''',N'''' pentamethyltriethylenetetramine;
N-(2-hydroxypropyl-butyl ether)-N,N',N'',N''',N'''' pentamethyltriethylenetetramine;
N-(2-hydroxypropyl-octadecyl ether)-N,N',N'',N''' tetramethyldiethylenetriamine;
N-(2-hydroxypropyl-hexadecyl ether)-N,N',N'',N''' tetramethyldiethylenetriamine;
N-(2-hydroxypropyl-tetradecyl ether)-N,N',N'',N''' tetramethyldiethylenetriamine;
N-(2-hydroxypropyl-dodecyl ether)-N,N',N'',N''' tetramethyldiethylenetriamine;
N-(2-hydroxypropyl-decyl ether)-N,N',N'',N''' tetramethyldiethylenetriamine;
N-(2-hydroxypropyl-octyl ether)-N,N',N'',N''' tetramethyldiethylenetriamine;
N-(2-hydroxypropyl-hexyl ether)-N,N',N'',N''' tetramethyldiethylenetriamine;
N-(2-hydroxypropyl-butyl ether)-N,N',N'',N''' tetramethyldiethylenetriamine; or any combination thereof.

A catalytically effective amount of the catalyst composition may be used in the polyurethane formulation. In one aspect, suitable amounts of the catalyst composition may range from about 0.01 to about 10 parts catalyst composition per 100 parts polyol by weight (pphp) in the polyurethane formulation, or from about 0.05 to about 2 pphp.

The hydroxyl functionality of catalyst compositions of the present invention enables the catalyst compositions to react with, and be immobilized into, the polyurethane matrix during and after polymerization. Furthermore, the reduced volatility, odor, and high molecular weight can limit the exposure of operators and end users to offensive amine vapors.

Polyols

Polyurethanes are produced from the polymerization reaction of organic isocyanate compounds with polyol hydroxyl groups. Catalyst compositions of the present invention are useful for catalyzing the reaction of isocyanates with active hydrogen-containing compounds such as polyols. Polyols suitable for use with the catalyst compositions of the present invention include, but are not limited to, polyalkylene ether polyols and polyester polyols. Polyalkylene ether polyols include poly(alkylene oxide) polymers such as poly(ethylene oxide) and poly(propylene oxide) polymers and copolymers with terminal hydroxyl groups derived from polyhydric compounds, including diols and triols; for example, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane, and similar low molecular weight polyols.

In one aspect of the present invention, a single high molecular weight polyether polyol may be used. Alternatively, a mixture of high molecular weight polyether polyols, for example, mixtures of di- and tri-functional materials and/or different molecular weight or different chemical composition materials may be used. Such di- and tri-functional materials include, but are not limited to ethyleneglycol, polyethyleneglycol, propyleneglycol, polypropyleneglycol, glycerine, glycerine-based polyether triols, trimethylolpropane, trimethylolpropane-based polyether triols, 1,3-butane diol, 1,4-butane diol, 1,6-hexane diol, neopentyl glycol, or any combination thereof.

Useful polyester polyols include, but are not limited to, those produced by reacting a dicarboxylic acid with an excess of a diol, for example, adipic acid with ethylene glycol or butanediol, or reaction of a lactone with an excess of a diol such as caprolactone with propylene glycol.

In addition to polyalkylene ether polyols and polyester polyols, polymer polyols are also suitable for use in the present invention. Polymer polyols are used in polyurethane foams to increase the foam's resistance to deformation, for example, to improve the load-bearing properties of the foam. Examples of polymer polyols include, but are not limited to, graft polyols or polyurea modified polyols (Polyharnstoff Dispersion polyols). Graft polyols comprise a triol in which vinyl monomers are graft copolymerized. Suitable vinyl monomers include, for example, styrene, or acrylonitrile. A polyurea modified polyol, is a polyol containing a polyurea dispersion formed by the reaction of a diamine and a diisocyanate in the presence of a polyol. A variant of polyurea modified polyols are polyisocyanate poly addition (PIPA) polyols, which are formed by the in situ reaction of an isocyanate and an alkanolamine in a polyol. Depending upon the load-bearing requirements, polymer polyols may comprise from about 20 to about 80 percent by weight of the total polyol content.

Blowing Agents

Polyurethane foams are typically produced from the reaction of isocyanates with a polyol in the presence of a blowing agent to produce voids in the polyurethane matrix during polymerization. Suitable blowing agents include, for example, inert compounds with low boiling points which are vaporized during the exothermic polymerization reaction. Such blowing agents are generally inert compounds that do not decompose or react during the polymerization reaction. The reaction exotherm is generally sufficient to vaporize the blowing agent, which then becomes entrapped in the polyurethane matrix, resulting in the formation of voids or cells. Optionally, additional heat can be added during the reaction to promote vaporization of the blowing agent. Examples of such blowing agents include, but are not limited to, chlorofluorocarbons, hydrogenated fluorocarbons, hydrogenated chlorofluorocarbons, low-boiling hydrocarbons such as cyclopentane, isopentane, or n-pentane, or any combination thereof.

A preferred blowing agent is water. Catalyst compositions of the present invention are useful for catalyzing the reaction of isocyanates with the water to produce carbon dioxide. As the carbon dioxide gas is produced, it becomes trapped in the polyurethane matrix, forming voids or cells.

Optional Additives

Catalyst compositions of the present invention can be used in conjunction with optional auxiliary components to produce polyurethane foams. Examples of auxiliary components include, but are not limited to, cell stabilizers, crosslinking agents, chain extenders, pigments, fillers, flame retardants, auxiliary gelling catalysts, auxiliary blowing catalysts, transition metal catalysts, or any combination thereof.

Cell stabilizers may include, for example, silicon surfactants or anionic surfactants. Examples of suitable silicon surfactants include, but are not limited to, polyalkylsiloxanes, polyoxyalkylene polyol-modified dimethylpolysiloxane, alkylene glycol-modified dimethylpolysiloxane, or any combination thereof. Suitable anionic surfactants include, but are not limited to, salts of fatty acids, salts of sulfuric acid esters, salts of phosphoric acid esters, sulfonates, or any combination thereof.

Suitable crosslinking agents include, but are not limited to, low-molecular compounds having at least two groups selected from a hydroxyl group, a primary amino group, a secondary amino group, or other active hydrogen-containing groups which are reactive with an isocyanate group. Crosslinking agents include, for example, polyhydric alcohols, polyamines, or any combination thereof. Non-limiting examples of suitable polyhydric alcohols include ethylene glycol, diethylene glycol, propylene glycol, dipropylene glycol, 1,4-butanediol, 1,6-hexanediol, neopentyl glycol, glycerol, trimethylolpropane, or any combination thereof. Non-limiting examples of polyamine crosslinkking agents include diethyltoluenediamine, chlorodiaminobenzene, diethanolamine, diisopropanolamine, triethanolamine, tripropanolamine, 1,6-hexanediamine, or any combination thereof.

Examples of chain extenders include, but are not limited to, compounds having hydroxyl or amino functional group, such as glycols, amines, diols, and water. Further non-limiting examples of chain extenders include ethylene glycol, propylene glycol, 1,4-butanediol, 1,3-butanediol, 1,5-pentanediol, 1,6-hexanediol, 1,10-decanediol, 1,12-dodecanediol, ethoxylated hydroquinone, 1,4-cyclohexanediol, N-methylethanolamine, N-methylisopropanolamine, 4-aminocyclohexanol, 1,2-diaminoethane, 2,4-toluenediamine, or any mixture thereof.

Pigments may be used to color code the polyurethane foams during manufacture to identify the product and/or grade of product or to conceal yellowing. Pigments may include any suitable organic or inorganic pigments. For example, organic pigments or colorants include, but are not limited to, azo/diazo dyes, phthalocyanines, dioxazines, or carbon black. Examples of inorganic pigments include, but are not limited to, titanium dioxide, iron oxides, or chromium oxide. Fillers may be used to increase the density and load bearing properties of polyurethane foams. Suitable fillers include, but are not limited to, barium sulfate or calcium carbonate. Flame retardants can be used to reduce the flammability of polyurethane foams. For example, suitable flame retardants include, but are not limited to, chlorinated phosphate esters, chlorinated paraffins, or melamine powders.

Auxiliary gelling catalysts may include, but are not limited to, diazabicyclooctane (triethylenediamine), supplied commercially as DABCO 33LV® catalyst by Air Products and Chemicals Inc.; quinuclidine and substituted quinuclidines; substituted pyrrolidines or pyrrolizidines; or N,N-dimethylaminoalkyl ureas and similar blends, suuplied commercially as DABCO® NE1070, DABCO® NE1060, DABCO® NE200, DABCO® NE400, DABCO® NE500, and DABCO® NE600.

Non-limiting examples of suitable auxiliary blowing catalysts include, bis-dimethylaminoethyl ether, commercially supplied as DABCO® BL-11 catalyst by Air Products and Chemicals, Inc.; pentamethyl-diethylenetriamine and related compositions; higher permethylated polyamines; 2-[N-(dimethylaminoethoxyethyl)-N-methylamino]ethanol and related structures; alkoxylated polyamines; imidazole-boron compositions; or amino propyl-bis(amino-ethyl)ether compositions. Catalysts compositions in accordance with the present invention may also be used in combination with transition metal catalysts, such as organotin catalysts.

Polyurethane Foams

Polyurethane foams can be produced by reacting any suitable organic isocyanate compounds with any suitable polyol compounds, as described in the art. Organic isocyanate compounds include, but are not limited to, hexamethylene diisocyanate (HDI), phenylene diisocyanate (PDI), toluene diisocyanate (TDI), and 4,4'-diphenylmethane diisocyanate (MDI). In one aspect of the invention, 2,4-TDI, 2,6-TDI, or a combination thereof may be used to produce polyurethane foams. Other suitable isocyanate compounds are mixtures of diisocyanates known commercially as "crude MDI", marketed as PAPI by Dow Chemical Company, which contains about 60% of 4,4'-diphenylmethane diisocyanate along with other isomeric and analogous higher polyisocyanates. Also suitable are "prepolymers" of these isocyanate compounds, comprising a partially prereacted mixture of a polyisocyanate and a polyether or polyester polyol.

Polyurethane foams produced using catalyst compositions of the present invention are comparable or superior to foams produced using catalyst compositions described in the prior art. For example, polyurethane foams produced with a catalyst composition in accordance with the present invention have reduced odor and decreased amine emissions.

A polyurethane foam produced in accordance with one aspect of the present invention, has an isocyanate index between about 70 and about 115 and comprises the following components by weight:

TABLE 1

Polyurethane Components

| Component | Percent by Weight |
| --- | --- |
| Polyol | 20-100 |
| Polymer polyol | 0-80 |
| Silicon surfactant | 1-2.5 |
| Blowing agent | 2-4.5 |
| Crosslinker | 0.5-2 |
| Catalyst composition | 0.25-2 |
| Polyisocyanate | 70-115 NCO Index |

The term "isocyanate index" (also commonly referred to as NCO index), is defined herein as the number of equivalents of isocyanate, divided by the total number of equivalents of active hydrogen, multiplied by 100. The NCO index is represented by the formula NCO index=[NCO/(OH+NH)]*100.

Although the present invention has been described as useful for preparing flexible polyurethane foams, the invention may also be employed to prepare semi-flexible and rigid polyurethane foams. Rigid polyurethane foams can be distinguished from flexible polyurethane foams by the presence of higher isocyanurate levels in the rigid foam. Flexible foams typically use polymer polyol as part of the overall polyol content in the foam composition, along with conventional triols of about 4000-5000 weight average molecular weight ($M_w$) and hydroxyl number (OH#) of about 28-35. In contrast, rigid polyurethane foam compositions use about 500-1000 Mw polyol with about 3-8 hydroxyl functionalities and OH# of about 160-700. Rigid foams can also be distinguished from the flexible foams by the isocyanate (NCO) index of the foam composition. Rigid foam compositions typically use a 100-300 NCO index whereas flexible foam compositions typically require a 70-115 NCO index.

For making lamination (insulation board) and appliance foams, the NCO index is typically from about 100 to about 300. For making open cell foam, the NCO index is typically from about 100 to about 120, and the foam is usually all water blown. Semiflexible molded foams have been utilized for many applications in the automotive area. The major applications are instrument panels and interior trims. The two main components are the base polyol and copolymer polyol (CPP). The base polyol is utilized at levels between about 70-100 pphp. The molecular weight of base polyols range from about 4500 to about 6000 for triols and from about 2000 to about 4000 for diols. Ethylene-oxide-capped polyether polyols have replaced most polyester polyols as the base polyol. The primary hydroxyl content is usually greater than about 75 wt % and the capping range is typically about 10-20 wt %. The other major component is CPP, which are used at levels up to about 20 wt %. The base polyol and CPP are blended with low molecular weight cross-linkers to build hardness and promote faster demolding. The level of cross-linker varies depending on the hardness requirement of the finished part. Water levels are chosen to give free rise densities from about 3 to about 6 pounds. Cell openers are also utilized in semiflexible foams to reduce the internal foam pressure during the cure cycle and thus reduce pressure-relief voids and "parting lines". Adhesion promoters can be added, depending upon the quality of the vinyl skin, to improve the adhesion between the polyurethane foam and the vinyl skin. The use of the catalyst composition of the present invention can reduce the discoloration of the vinyl skin typically observed with conventional amine catalysts because the N—H group of the amide functionality can react with the isocyanate to form a covalent bond with the polyurethane polymer.

As described in the examples below, the foams made with the reactive catalyst composition are of the same or superior quality as the foams made with the industry standard. Also, catalyst compositions in accordance with the present invention provide the following advantages: low amine emissions in the finished polyurethane product; low tertiary amine catalyst vapor pressure; low odor of the finished polyurethane product; effective immobilization of the tertiary amine catalyst during and after polymerization; lower amine concentration in the finished polyurethane product; and optimum physical polyurethane foam properties, such as reduced force-to-crush values.

EXAMPLES

The following examples are presented for purposes of illustration, and are not intended to impose limitations on the scope of the invention.

Example 1

Synthesis of N-[2-hydroxypropyl-(2-ethylhexyl)-ether]-N,N',N'',N''',N'''' pentamethyltriethylenetetramine A sample of about 100 grams (0.647 mole) of commercially available triethylenetetramine (about 67 weight % TETA) was charged into a 500 mL three-necked round bottom flask equipped with a Teflon® coated magnetic stir bar and a pressure equalizing dropping funnel. The amine was heated to about 80° C. and pressurized with nitrogen. About 60.2 g (0.32 moles) of 2-ethylhexyl glycidyl ether (commercially available from Air Products and Chemicals as Epodil® 746) was slowly added to the flask over a period of thirty minutes. A mild exotherm was observed during the addition, causing the temperature to rise to about 84° C. After the end of the addition, the mixture was heated to about 120° C. and maintained at that temperature for about thirty minutes. The product was collected and distilled under vacuum to remove unreacted TETA (about 59.0 g). The crude product (about 99.3 g) was dissolved in methanol and placed in a reactor together with about 20 g of 5% palladium on carbon catalyst. The reactor was pressurized with hydrogen and heated up to about 80° C. Formalin (37 % formaldehyde in water) was slowly added while the hydrogen pressure was monitored. At the end of the addition the reaction was kept at about 80° C. for approximately thirty minutes. The product was filtered and methanol and water were removed from the product by distillation to yield a mixture containing N-[2-hydroxpropyl-2-(ethylhexyl)-ether]-N,N',N'',N''',N'''' pentamethyltriethylenetetramine.

Example 2

Synthesis of N-[2-hydroxypropyl-(dodecyl)-ether]-N,N',N'',N''',N'''' pentamethyltriethylenetetramine and N-[2-hydroxypropyl-(tetradecyl)-ether]-N,N',N'',N''', N'''' pentamethyltriethylenetetramine A sample of about 100 g (0.647 mole) of commercially available triethylenetetramine (about 67 weight % TETA) was charged into a 500 mL three-necked round bottom flask equipped with a Teflon® coated magnetic stir bar and a pressure equalizing dropping funnel. The amine was heated to about 80° C. and pressurized with nitrogen. About 87.3 g (0.32 moles) of a commercially available mixture of dodecyl/tetradecyl glycidyl ether (commercially available from Air Products and Chemicals as Epodil® 748) was slowly added to the flask over a period of thirty minutes. A mild exotherm was observed during the addition, causing the temperature to rise to about 84° C. After the end of the addition, the mixture was heated to about 120° C. and maintained at that temperature for about thirty minutes. The product was collected and distilled under vacuum to remove unreacted TETA (about 53.3 g). The crude product (about 132.1 g) was dissolved in methanol and placed in a reactor together with 20 g of 5% palladium on carbon catalyst. The reactor was pressurized with hydrogen and heated up to about 80° C. Formalin (37% formaldehyde in water) was slowly added while the hydrogen pressure was monitored. At the end of the addition the reaction was kept at about 80° C. for approximately thirty minutes. The product was filtered and methanol and water were removed from the product by distillation to yield a mixture containing N-[2-hydroxypropyl-(dodecyl)-ether]-N,N',N'',N''',N'''' pentamethyltriethylenetetramine and N-[2-hydroxypropyl-(tetradecyl)-ether]-N,N',N'',N''',N'''' pentamethyltriethylenetetramine.

Example 3

Rate of Rise of Polyurethane Foams

Four foams were prepared. Foam A was prepared using bis-dimethylaminoethylether (DABCO® BL-11). Foam B was prepared using 2-[N-(dimethylaminoethoxyethyl)-N-methylamino]ethanol (DMAEE-NM-EA). Foam C was prepared using N-[2-hydroxypropyl-2-(ethylhexyl)-ether]-N,N',N'',N''',N'''' pentamethyltriethylenetetramine (Example 1). Foam D was prepared using a mixture of N-[2-hydroxypropyl-(dodecyl)-ether]-N,N',N'',N''',N'''' pentamethyltriethylenetetramine and N-[2-hydroxypropyl-(tetradecyl)-ether]-N,N',N'',N''',N'''' pentamethyltriethylenetetramine (Example 2).

For each foam, the catalyst was added to about 192 g of the premix (described in Table 2) in a 32 oz (951 mL) paper cup. The formulation was mixed for about 10 seconds at about 6,000 RPM using an overhead stirrer fitted with a 2 in (5.1 cm) diameter stirring paddle.

TABLE 2

Premix Components (Example 3)

| Component | Percent by Weight |
|---|---|
| Polyol 1 | 50 |
| Polyol 2 | 50 |
| Water | 2.34 |
| Silicon surfactant | 0.75 |
| DABCO 33-LV ® | 0.25 |
| DABCO ® BL-11 | 0.10 |
| Crosslinker | 1.76 |

Toluene diisocyanate was added in an amount sufficient to produce a foam with an isocyanate index of approximately 100. The formulation was mixed well for about 6 seconds at about 6,000 RPM using the same stirrer. The 32 oz cup was dropped through a hole in the bottom of a 128 oz (3804 mL) paper cup on a stand. The hole was sized to catch the lip of the 32 oz cup. The total combined volume of the paper cups was about 160 oz (4755 ml). Foams approximated this volume at the end of the foaming process. Maximum foam height was recorded. A comparison of the properties of Foam A and Foam B is presented below in Tables 3 and 4.

TABLE 3

Foam Comparison (Example 3)

| PARAMETER | FOAM A "DABCO BL-11" | FOAM B "DMAEE-NM-EA" | FOAM C "Example 1" | FOAM D "Example 2" |
|---|---|---|---|---|
| Amount of DABCO 33-LV ®[1] (pphp) | 0.32 | — | — | — |
| Amount of DABCO ® BL-11[2] (pphp) | 0.08 | — | — | — |
| Amount of DABCO ® NE1060[3] (pphp) | — | 0.70 | 0.70 | 0.70 |
| Amount of DMAEE-NM-EA[4] (pphp) | — | 0.15 | — | — |
| Amount of Example 1 catalyst (pphp) | — | — | 0.40 | — |
| Amount of Example 2 catalyst (pphp) | — | — | — | 0.40 |
| Cream (sec) | 8.30 | 7.80 | 7.30 | 8.30 |
| Cup 1 (sec) | 15.70 | 13.60 | 13.30 | 13.60 |

TABLE 3-continued

Foam Comparison (Example 3)

| PARAMETER | FOAM A "DABCO BL-11" | FOAM B "DMAEE-NM-EA" | FOAM C "Example 1" | FOAM D "Example 2" |
|---|---|---|---|---|
| String gel (sec) | 68.70 | 69.80 | 69.50 | 71.20 |
| Full rise (mm) | 126.20 | 116.60 | 116.60 | 108.80 |

[1]DABCO 33-LV ® is a commercially available catalyst supplied by Air Products & Chemicals [33% solution of triethylenediamine in dipropylene glycol]
[2]DABCO ® B-11 is a commercially available catalyst supplied by Air Products & Chemicals [70% solution of bis-dimethylaminoethylether in dipropylene glycol]
[3]DABCO ® NE1060 is a commercially available catalyst supplied by Air Products & Chemicals [75% dipropylene glycol solution of N-(3-dimethylaminopropyl)-urea (87%) and N,N'-bis-(3-dimethylaminopropyl)-urea (13%)]
[4]DMAEE-NM-EA or 2-[N-(dimethylaminoethoxyethyl)-N-methylamino]ethanol is a commercially available catalyst supplied by Air Products & Chemicals

TABLE 4

Foam Comparison (Example 3)

| PARAMETER | FOAM A "DABCO BL-11" | FOAM B "DMAEE-NM-EA" | FOAM C "Example 1" | FOAM D "Example 2" |
|---|---|---|---|---|
| Amount of catalyst (pphp) | 0.08 | 0.15 | 0.40 | 0.40 |
| Amount of catalyst (mol × $10^3$) | 0.5 | 0.80 | 0.99 | 0.82 |
| Catalyst molecular weight ($M_w$) | 160 | 190 | 402 | 486 |
| Mixing time (sec) | 12 | 12 | 12 | 12 |
| Test time (sec) | 300 | 300 | 300 | 300 |
| Rise height (mm) | 406.2 | 403.0 | 405.7 | 398.8 |
| Rise time (sec) | 89.2 | 81.8 | 80.4 | 75.6 |
| Maximum height (mm) | 411.9 | 408.6 | 411.4 | 404.3 |
| Final height (mm) | 407.7 | 402.5 | 408.3 | 399.1 |
| Shrinkage (%) | 1.5 | 2.2 | 1.1 | 1.9 |

As shown in Tables 3 and 4, under similar reaction conditions catalysts of the present invention have activities comparable to standard catalysts (DABCO BL-11® and DMAEE-NM-EA). Furthermore, foam appearance and percent shrinkage were essentially identical, showing that catalyst compositions of the present invention do not exhibit either diminished reactivity as compared to standard catalysts or diminished foam quality as compared to foam produced by standard catalysts.

Example 4

Physical Properties of Polyurethane Foams

Automotive cushions were produced using the catalysts of Examples 1 and 2 and a DABCO® NE 1060 catalyst as an auxiliary gelling catalyst. Two foams, Foam E [using Example 1 catalyst] and Foam F [using Example 2 catalyst] were made in a heated test block mold at about 65° C. The force-to-crush (FTC) results were obtained using a mechanical device equipped with a 1,000 lb (453.6 kg) capacity pressure transducer mounted between the 50 square inch (322.6 cm$^2$) circular plate and the drive shaft. The Dayton motor specifications, model 4Z528, includes a ⅙ horsepower (124.3 J/s) with an F/L rpm of 1800 and an F/L torque of 5.63 in-lb (6.36×$10^4$ N$_m$).

The foam pads were compressed to 50% of their original thickness and the force necessary to achieve the compression was measured and recorded in whole pounds (Newtons). The device used mimics the ASTM D-3574, Indentation Force Deflection Test, and provides a numerical value for one minute post demolded foam initial hardness or softness. As shown in Table 5, lower FTC values are obtained from foams produced with amine catalysts having surface active groups.

TABLE 5

Force-to-Crush Comparison (Example 4)

| PARAMETER | FOAM E | FOAM F |
|---|---|---|
| Amount of catalyst (pphp) | 0.40 | 0.40 |
| Amount of DABCO ® NE1060 (pphp) | 0.70 | 0.70 |
| Force to crush (N) | 180 | 139 |

Example 5

Rate of Rise and Physical Properties of Polyurethane Foams

Three foams, Foam G [using Example 1 catalyst], Foam H [using Example 2 catalyst], and Foam I [using DABCO BLV®, a commercially available catalyst from Air Products and Chemicals. For each foam, the catalyst was added to 339.2 g of the premix (described in Table 6) in a 32 oz (951 mL) paper cup. The formulation was mixed for about 10 seconds at about 6,000 RPM using an overhead stirrer fitted with a 2 in (5.1 cm) diameter stirring paddle.

TABLE 6

Premix Components (Example 5)

| Component | Percent by Weight |
|---|---|
| VORANOL 3512A ®[5] | 100.00 |
| Water | 4.60 |
| DABCO ®DC 5982[6] | 0.90 |
| DABCO ® T-10[7] | 0.42 |
| TDI | 56.20 |

[5]VORANOL 3512A ® is a commercially available polyol supplied by Dow Chemicals
[6]DABCO ® DC5982 is a commercially available silicon surfactant supplied by Air Products and Chemicals
[7]DABCO ® T-10 is a commercially available tin catalyst provided by Air Products and Chemicals Toluene diisocyanate was added in an amount sufficient to produce a foam with an NCO index of approximately 108. The formulation was mixed well for about 6 seconds at about 6,000 RPM using the same stirrer. The contents of the paper cup were poured into a 3.5 gallon container. Foams approximated this volume at the end of the foaming process. The rate of rise was recorded and the physical properties were evaluated. A comparison of the properties of Foams G, H, and I is presented below in Tables 7 and 8.

TABLE 7

Foam Comparison (Example 5)

| PARAMETER | FOAM G | FOAM H | FOAM I |
|---|---|---|---|
| Amount of catalyst (pphp) | 0.20 | 0.24 | 0.12 |
| Amount of catalyst (moles × $10^3$) | 0.6 | 0.5 | 0.8 |
| Mixing time (sec) | 12 | 12 | 12 |
| Test time (sec) | 300 | 300 | 300 |
| Rise height (mm) | 307.9 | 308.4 | 303.9 |
| Rise time (sec) | 114.0 | 126.4 | 112.4 |
| Maximum height (mm) | 314.2 | 314.5 | 310.1 |
| Final height (mm) | 314.2 | 314.5 | 310.0 |
| Shrinkage (%) | 2.7 | 2.9 | 2.4 |

TABLE 8

Physical Properties of Foams (Example 5)

| PARAMETER | FOAM G | FOAM H | FOAM I |
|---|---|---|---|
| Amount of catalyst (pphp) | 0.20 | 0.24 | 0.12 |
| Amount of catalyst (moles × $10^3$) | 0.6 | 0.5 | 0.8 |
| Tear strength ($lb_f$) | 2.30 ± 0.32 | 2.10 ± 0.22 | 2.14 ± 0.24 |
| Tensile strength (psi) | 14.0 ± 0.36 | 13.0 ± 1.49 | 13.7 ± 0.65 |
| Density ($lb/ft^3$) | 1.38 ± 0.104 | 1.40 ± 0.096 | 1.41 ± 0.054 |
| Percent break elongation | 104.0 ± 23 | 98.1 ± 15.2 | 101.7 ± 23 |
| Air flow (scfm) | 1.54 ± 0.41 | 3.47 ± 0.84 | 2.15 ± 0.62 |
| 50% HACS | 6.71 ± 1.76 | 6.18 ± 1.81 | 6.02 ± 3.00 |
| 50% CS | 3.82 ± 1.21 | 4.48 ± 1.89 | 3.39 ± 1.13 |

Example 6

Chemical Analysis of N-[2-hydroxypropyl-(2-ethylhexyl)-ether]-N,N',N'',N''',N''' pentamethyltriethylenetetramine The catalyst composition from Example 1 was analyzed by Gas Chromatography-Mass Spectrometry (GC-MS) using a Finnigan SSQ7000 single quadrupole mass spectrometer connected to a Varian 3400 gas chromatograph. A 30M× 0.25mm ID crosslinked (5% phenyl) methylpolysiloxane capillary column with a 0.1 μm film thickness was used for component separation. Helium was used as the carrier gas. The sample was analyzed in Electron Ionization (EI) mode with electron energy of 70 eV to obtain fragmentation for structure identification. The sample was also analyzed in Chemical Ionization (CI) mode using ammonia as the chemical ionization gas to obtain molecular weights. The CI analysis was repeated using ammonia-$d_3$ to determine the number of labile hydrogens for the compounds of interest.

The major components identified in the sample were the 1:1 products of TETA reacting with 2-ethylhexyl glycidyl ether. Because TETA is a mixture of 5 linear and cyclic compounds, eight isomers of 1:1 products are possible. All eight isomers were observed in the sample. The components have the structures given below.

Component A

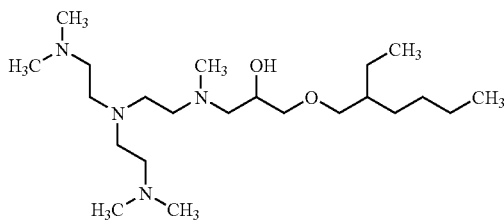

Component B

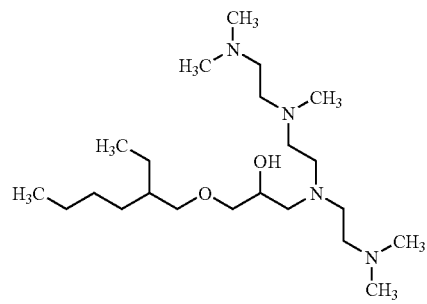

-continued
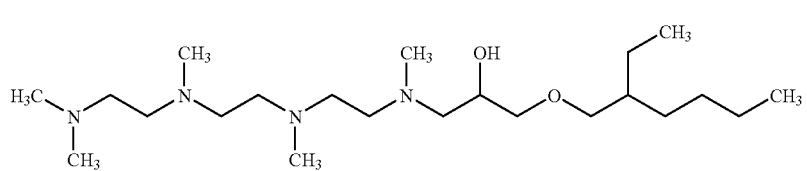
Component C
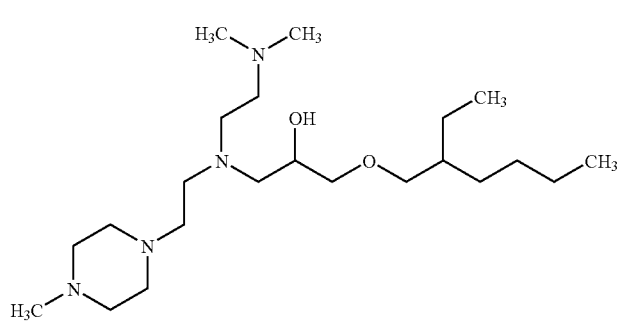
Component D
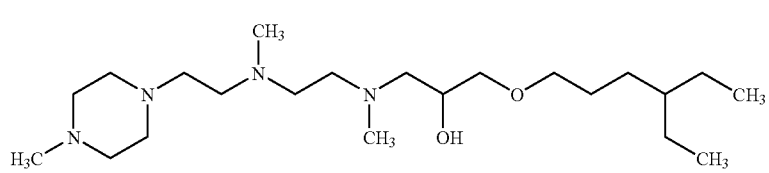
Component E
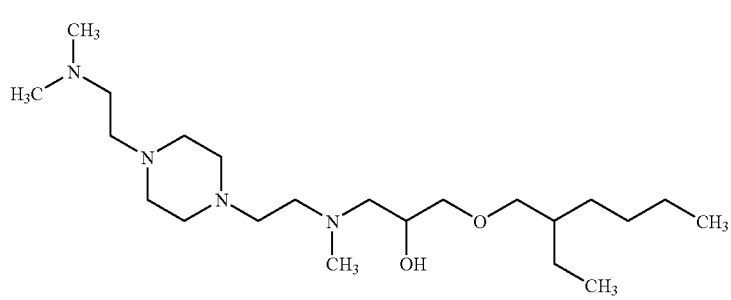
Component F
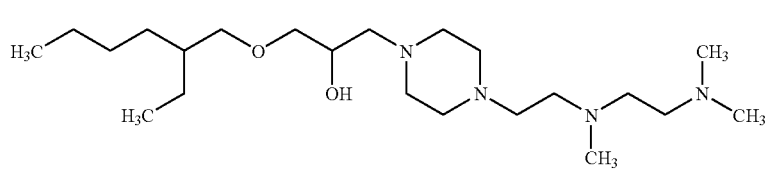
Component G
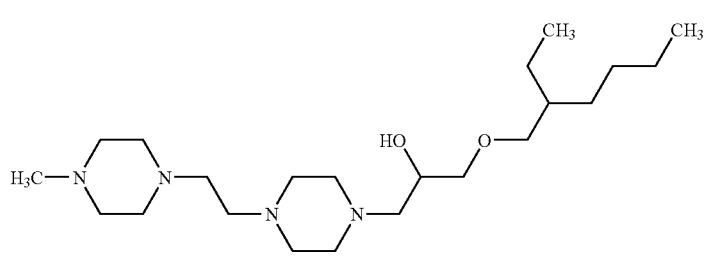
Component H The approximated distribution of these eight 1:1 isomer products is indicated below in Table 9, as calculated by peak area percentage.

TABLE 9

Isomer Product Distribution (Example 6)

| Component | Distribution (%) |
|---|---|
| Component A | <0.5% |
| Component B | 29.4% |
| Component C | 36.6% |
| Component D | 3.4% |
| Component E | 5.0% |
| Component F | 10.4% |
| Component G | 15.7% |
| Component H | 1.4% |

Various 1:2 (TETA:glycidyl ether) isomers were observed in the GC-MS analysis. These components had molecular weights of about 574 and about 572 daltons. Due to the volatility of the compounds being analyzed, it is difficult to observe the 1:2 products, and any 1:3 or 1:4 products are not observed. In order to determine the distribution of the TETA: glycidyl ether addition, a Matrix Assisted Laser Desorption Ionization (MALDI) Mass Spectrometric analysis was performed. The MALDI experiment was carried out on a Bruker Biflex TOFMS. The sample was prepared in methanol and mixed with an approximately 0.25M 2,5-dihydrobenzoic acid matrix solution. The sample as irradiated with a $N_2$ laser and positive ions were analyzed via TOFMS. Clusters of peaks representing the 1:1, 1:2, and 1:3 TETA/glycidyl ether components were observed. No 1:4 TETA/glycidyl ether components were detected using this method. The distribution of the three groups as seen by MALDI analysis is indicated below in Table 10.

TABLE 10

Isomer Group Distribution (Example 6)

| Component | Distribution (%) |
|---|---|
| 1:1 | 81.7% |
| 1:2 | 15.8% |
| 1:3 | 2.6% |

Example 7

Chemical Analysis of N-[2-hydroxypropyl-(dodecyl)-ether]-N,N',N'',N''',N'''' pentamethyltriethylenetetramine and N-[2-hydroxypropyl-(tetradecyl)-ether]-N,N',N'',N''',N'''' pentamethyltriethylenetetramine The catalyst composition from Example 2 was analyzed as indicated in Example 6. The major components identified in the sample were the 1:1 products of TETA reacting with dodecyl/tetradecyl glycidyl ether. Seven of the eight possible 1:1 isomer products were observed in the GC-MS analysis. The one isomer not observed using this method (Component I), probably because of its very low concentration, is a structure analogous to Component A from Example 6. The components have the structures given below.

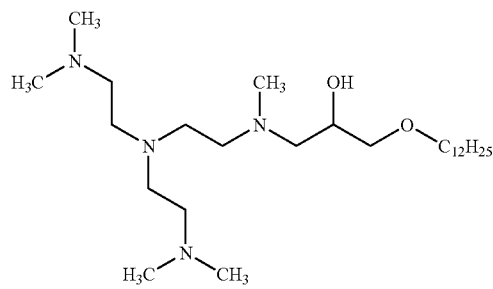

Component I

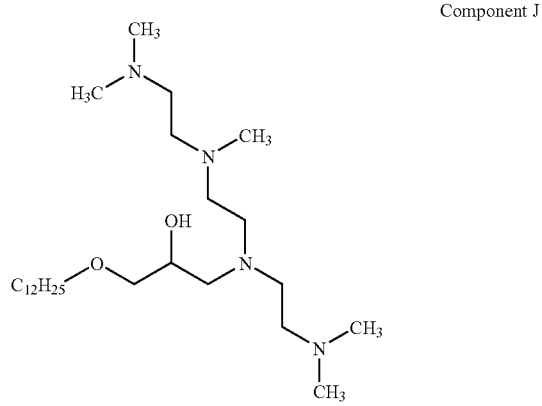

Component J

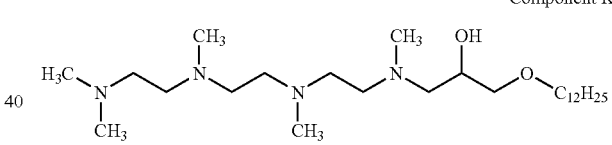

Component K

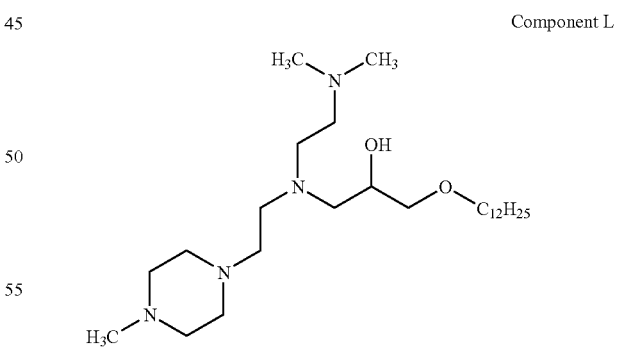

Component L

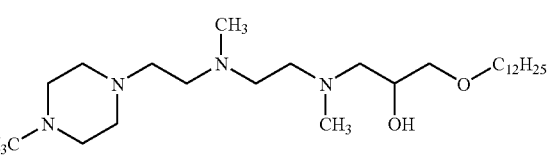

Component M

-continued

Component N

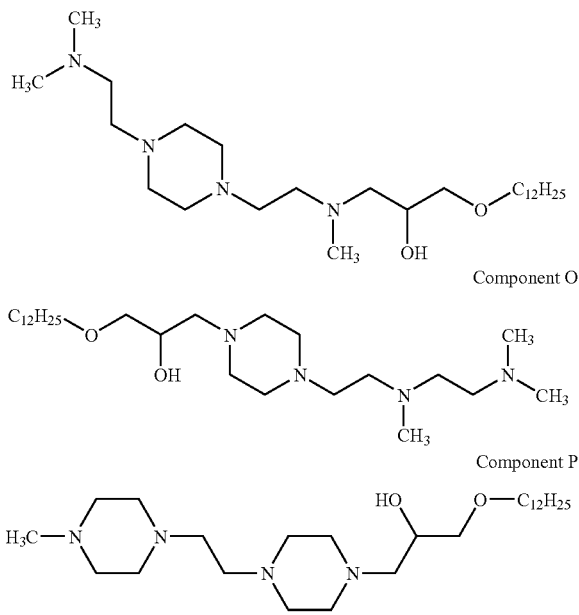

Component O

Component P

The approximated distribution of these eight 1:1 isomer products is indicated below in Table 11, as calculated by peak area percentage.

TABLE 11

Isomer Product Distribution (Example 7)

| Component | Distribution (%) |
|---|---|
| Component I | NA |
| Component J | 31.1% |
| Component K | 44.5% |
| Component L | 2.4% |
| Component M | 3.6% |
| Component N | 6.6% |
| Component O | 11.0% |
| Component P | 0.8% |

Clusters of peaks representing the 1:1, 1:2 TETA/glycidyl ether components were observed using a MALDI analysis. The distribution of these groups as seen by MALDI analysis is indicated below in Table 12.

TABLE 12

Isomer Group Distribution (Example 7)

| Component | Distribution (%) |
|---|---|
| 1:1 | 83.1% |
| 1:2 | 16.2% |

The invention is claimed:

1. A compound having the general formula

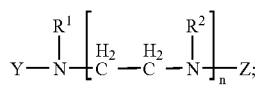

wherein
R$^1$ and R$^2$ are methyl;
Y is methyl
Z is

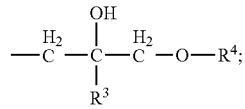

R$^3$ is hydrogen;
R$^4$ is a substituted or unsubstituted alkyl group having from 1 to about 36 carbon atoms, or a substituted or unsubstituted alkenyl group having from 1 to about 36 carbon atoms; and
n is an integer from 2 to 3, inclusive.

2. A compound according to claim 1, wherein R$^4$ is a substituted or unsubstituted alkyl group having from 1 to about 18 carbon atoms, or a substituted or unsubstituted alkenyl group having from 1 to about 18 carbon atoms.

3. A compound according to claim 1, wherein the compound is
N-(2-hydroxypropyl-octadecyl ether)-N,N',N'',N''',N'''' pentamethyltriethylenetetramine;
N-(2-hydroxypropyl-heptadecyl ether)-N,N',N'',N''',N'''' pentamethyltriethylenetetramine;
N-(2-hydroxypropyl-hexadecyl ether)-N,N',N'',N''',N'''' pentamethyltriethylenetetramine;
N-(2-hydroxypropyl-pentadecyl ether)-N,N',N'',N''',N'''' pentamethyltriethylenetetramine;
N-(2-hydroxypropyl-tetradecyl ether)-N,N',N'',N''',N'''' pentamethyltriethylenetetramine;
N-(2-hydroxypropyl-tridecyl ether)-N,N',N'',N''',N'''' pentamethyltriethylenetetramine;
N-(2-hydroxypropyl-dodecyl ether)-N,N',N'',N''',N'''' pentamethyltriethylenetetramine;
N-(2-hydroxypropyl-undecyl ether)-N,N',N'',N''',N'''' pentamethyltriethylenetetramine;
N-(2-hydroxypropyl-decyl ether)-N,N',N'',N''',N'''' pentamethyltriethylenetetramine;
N-(2-hydroxypropyl-nonyl ether)-N,N',N'',N''',N'''' pentamethyltriethylenetetramine;
N-(2-hydroxypropyl-octyl ether)-N,N',N'',N''',N'''' pentamethyltriethylenetetramine;
N-(2-hydroxypropyl-heptyl ether)-N,N',N'',N''',N'''' pentamethyltriethylenetetramine;
N-(2-hydroxypropyl-hexyl ether)-N,N',N'',N''',N'''' pentamethyltriethylenetetramine;
N-(2-hydroxypropyl-pentyl ether)-N,N',N'',N''',N'''' pentamethyltriethylenetetramine;
N-(2-hydroxypropyl-butyl ether)-N,N',N'',N''',N'''' pentamethyltriethylenetetramine;
N-(2-hydroxypropyl-ethyl ether)-N,N',N'',N''',N'''' pentamethyltriethylenetetramine;
N-(2-hydroxypropyl-methyl ether)-N,N',N'',N''',N'''' pentamethyltriethylenetetramine;
N-(2-hydroxypropyl-octadecyl ether)-N,N',N'',N''' tetramethyldiethylenetriamine;
N-(2-hydroxypropyl-heptadecyl ether)-N,N',N'',N''' tetramethyldiethylenetriamine;
N-(2-hydroxypropyl-hexadecyl ether)-N,N',N'',N''' tetramethyldiethylenetriamine;
N-(2-hydroxypropyl-pentadecyl ether)-N,N',N'',N''' tetramethyldiethylenetriamine;

N-(2-hydroxypropyl-tetradecyl ether)-N,N',N",N''' tetramethyldiethylenetriamine;
N-(2-hydroxypropyl-tridecyl ether)-N,N',N",N''' tetramethyldiethylenetriamine;
N-(2-hydroxypropyl-dodecyl ether)-N,N',N",N''' tetramethyldiethylenetriamine;
N-(2-hydroxypropyl-undecyl ether)-N,N',N",N''' tetramethyldiethylenetriamine;
N-(2-hydroxypropyl-decyl ether)-N,N',N",N''' tetramethyldiethylenetriamine;
N-(2-hydroxypropyl-nonyl ether)-N,N',N",N''' tetramethyldiethylenetriamine;
N-(2-hydroxypropyl-octyl ether)-N,N',N",N''' tetramethyldiethylenetriamine;
N-(2-hydroxypropyl-heptyl ether)-N,N',N",N''' tetramethyldiethylenetriamine;
N-(2-hydroxypropyl-hexyl ether)-N,N',N",N''' tetramethyldiethylenetriamine;
N-(2-hydroxypropyl-pentyl ether)-N,N',N",N''' tetramethyldiethylenetriamine;
N-(2-hydroxypropyl-butyl ether)-N,N',N",N''' tetramethyldiethylenetriamine;
N-(2-hydroxypropyl-ethyl ether)-N,N',N",N''' tetramethyldiethylenetriamine;
N-(2-hydroxypropyl-methyl ether)-N,N',N",N''' tetramethyldiethylenetriamine; or any combination thereof.

4. A compound according to claim 3, wherein the compound is
N-(2-hydroxypropyl-octadecyl ether)-N,N',N",N''',N'''' pentamethyltriethylenetetramine;
N-(2-hydroxypropyl-hexadecyl ether)-N,N',N",N''',N'''' pentamethyltriethylenetetramine;
N-(2-hydroxypropyl-tetradecyl ether)-N,N',N",N''',N'''' pentamethyltriethylenetetramine;
N-(2-hydroxypropyl-dodecyl ether)-N,N',N",N''',N'''' pentamethyltriethylenetetramine;
N-(2-hydroxypropyl-decyl ether)-N,N',N",N''',N'''' pentamethyltriethylenetetramine;
N-(2-hydroxypropyl-octyl ether)-N,N',N",N''',N'''' pentamethyltriethylenetetramine;
N-(2-hydroxypropyl-hexyl ether)-N,N',N",N''',N'''' pentamethyltriethylenetetramine;
N-(2-hydroxypropyl-butyl ether)-N,N',N",N''',N'''' pentamethyltriethylenetetramine;
N-(2-hydroxypropyl-octadecyl ether)-N,N',N",N''' tetramethyldiethylenetriamine;
N-(2-hydroxypropyl-hexadecyl ether)-N,N',N",N''' tetramethyldiethylenetriamine;
N-(2-hydroxypropyl-tetradecyl ether)-N,N',N",N''' tetramethyldiethylenetriamine;
N-(2-hydroxypropyl-dodecyl ether)-N,N',N",N''' tetramethyldiethylenetriamine;
N-(2-hydroxypropyl-decyl ether)-N,N',N",N''' tetramethyldiethylenetriamine;
N-(2-hydroxypropyl-octyl ether)-N,N',N",N''' tetramethyldiethylenetriamine;
N-(2-hydroxypropyl-hexyl ether)-N,N',N",N''' tetramethyldiethylenetriamine;
N-(2-hydroxypropyl-butyl ether)-N,N',N",N''' tetramethyldiethylenetriamine; or any combination thereof.

5. A compound according to claim 4, wherein the compound is a mixture of
N-[2-hydroxypropyl-(dodecyl)-ether]-N,N',N",N''',N'''' pentamethyltriethylenetetramine and
N-[2-hydroxypropyl-(tetradecyl)-ether]-N,N',N",N''',N'''' pentamethyltriethylenetetramine.

6. A compound according to claim 1, wherein the compound is produced by reacting an alkyl glycidyl ether with an ethyleneamine.

7. A compound according to claim 6, wherein the alkyl glycidyl ether is octadecyl glycidyl ether, heptadecyl glycidyl ether, hexadecyl glycidyl ether, pentadecyl glycidyl ether, tetradecyl glycidyl ether, tridecyl glycidyl ether, dodecyl glycidyl ether, undecyl glycidyl ether, decyl glycidyl ether, nonyl glycidyl ether, octyl glycidyl ether, heptyl glycidyl ether, hexyl glycidyl ether, pentyl glycidyl ether, butyl glycidyl ether, ethyl glycidyl ether, methyl glycidyl ether, or any combination thereof.

8. A compound according to claim 6, wherein the ethyleneamine is diethylenetriamine or triethylenetetramine.

9. A method to produce a compound having the general formula $$Y-N\begin{matrix}R^1\\|\\\phantom{N}\end{matrix}\left[\begin{matrix}\phantom{R}\\H_2\\C\end{matrix}-\begin{matrix}\phantom{R}\\H_2\\C\end{matrix}-\begin{matrix}R^2\\|\\N\end{matrix}\right]_n-Z,$$

wherein
$R^1$ and $R^2$ are methyl;
Y is methyl
Z is $$-\begin{matrix}H_2\\C\end{matrix}-\begin{matrix}OH\\|\\C\\|\\R^3\end{matrix}-\begin{matrix}H_2\\C\end{matrix}-O-R^4;$$

$R^3$ is hydrogen;
$R^4$ is a substituted or unsubstituted alkyl group having from 1 to about 36 carbon atoms, a substituted or unsubstituted alkenyl group having from 1 to about 36 carbon atoms; and
n is an integer from 2 to 3, inclusive;
the method comprising reacting an alkyl glycidyl ether with an ethyleneamine.

10. A method according to claim 9, wherein the alkyl glycidyl ether has an alkyl group having from 1 to about 35 carbon atoms.

11. A method according to claim 10, wherein the alkyl group is octadecyl, heptadecyl, hexadecyl, pentadecyl, tetradecyl, tridecyl, dodecyl, undecyl, decyl, nonyl, octyl, heptyl, hexyl, pentyl, butyl, ethyl, or methyl.

12. A method according to claim 9, wherein the ethyleneamine is diethylenetriamine or triethylenetetramine.

* * * * *